(12) United States Patent
Cronin

(10) Patent No.: US 6,635,055 B1
(45) Date of Patent: Oct. 21, 2003

(54) MICROWAVE APPLICATOR FOR ENDOMETRIAL ABLATION

(75) Inventor: Nigel Cronin, Bath (GB)

(73) Assignee: Microsulis PLC, Hampshire (GB)

( * ) Notice: Subject to any disclaimer, the term of this patent is extended or adjusted under 35 U.S.C. 154(b) by 0 days.

(21) Appl. No.: 09/674,783

(22) PCT Filed: May 5, 1998

(86) PCT No.: PCT/GB99/01398

§ 371 (c)(1),
(2), (4) Date: Dec. 13, 2000

(87) PCT Pub. No.: WO99/56642

PCT Pub. Date: Nov. 11, 1999

(30) Foreign Application Priority Data

May 6, 1998 (GB) ............................................. 9809539

(51) Int. Cl.$^7$ ........................... A61B 18/04; H01P 5/103
(52) U.S. Cl. ............................ 606/33; 607/156; 333/26
(58) Field of Search ........................... 333/26; 606/33; 607/156

(56) References Cited

FOREIGN PATENT DOCUMENTS

| DE | 2815156 A | | 10/1978 | |
|---|---|---|---|---|
| RU | 1376138 | * | 2/1988 | ............. 333/26 |
| RU | 3724945 | * | 2/1989 | ............. 333/26 |
| WO | WO 95 04385 A | | 2/1995 | |

* cited by examiner

Primary Examiner—Benny T. Lee
(74) Attorney, Agent, or Firm—Reising, Ethington, Barnes, Kisselle, P.C.

(57) ABSTRACT

A microwave applicator for applying electromagnetic radiation at microwave frequency includes a coaxial input for a microwave signal input and a waveguide for receiving and propagating the microwave signal input. Dielectric material is positioned within the waveguide and extends beyond the waveguide to form an antenna for radiating microwave energy. The coaxial input has direct in-line transition to the dielectric-filled waveguide. Preferably, this direct in-line transition is achieved by the central conductor of the coaxial input extending axially centrally into the waveguide so as to excite microwaves in the waveguide. A lateral conductor extends radially from the central conductor to assist the launch of the microwaves into the waveguide. Preferably, the applicator includes a temperature sensor which is directly connected to the coaxial input.

17 Claims, 2 Drawing Sheets

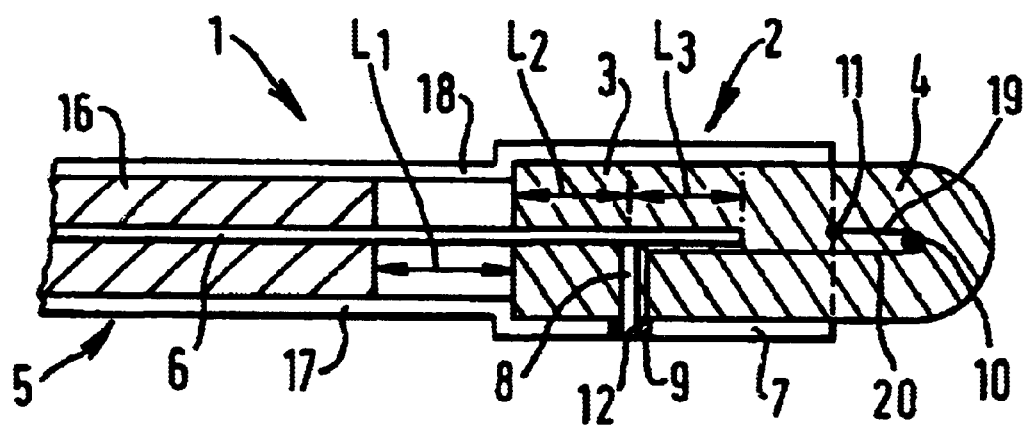
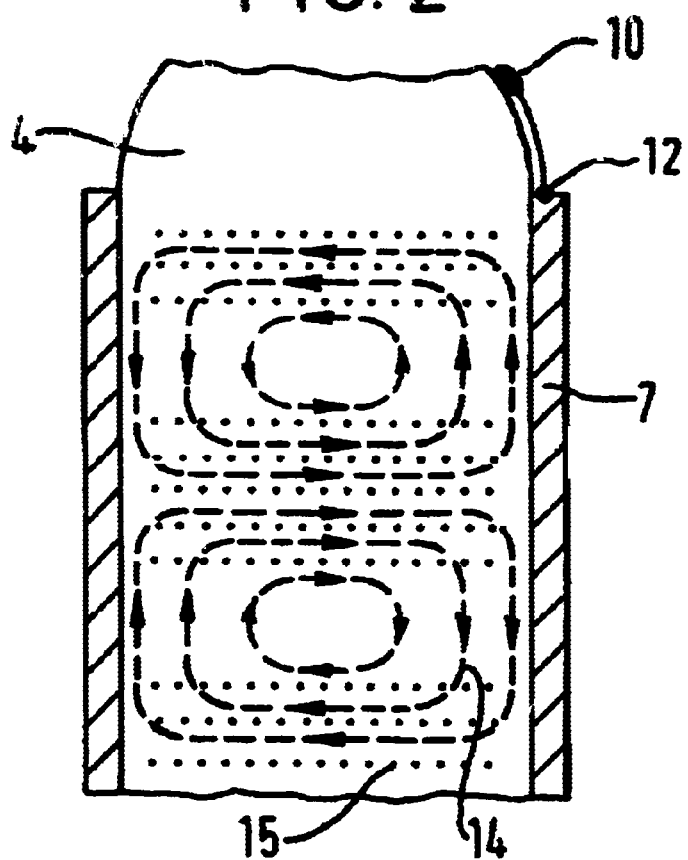

MICROWAVE APPLICATOR FOR ENDOMETRIAL ABLATION

TECHNICAL FIELD

This invention relates to a microwave applicator for the treatment of a body by means of microwave electromagnetic energy. The body is preferably biological tissue and, preferably, the applicator is for use in the treatment of menorrhagia.

Menorrhagia is a common condition in women over the age of forty and manifests itself as excessive bleeding from the endometrium which constitutes the inner wall of the uterus.

The most common form of treatment is to carry out a hysterectomy in which the entire uterus is removed.

In our earlier application published under number WO95/04385, the contents of which are incorporated herein by reference, we disclosed a probe for applying electromagnetic radiation at microwave frequency which comprised a dielectric-filled waveguide with an exposed portion at the tip defining an antenna. However, in several of the embodiments, the microwaves were launched in a first air-filled waveguide and then the microwaves were passed into a second waveguide which contained the dielectric material. Between the waveguides, a tapered waveguide provided a transition. The dielectric filled waveguide was of smaller diameter than the air-filled waveguide because, at a given frequency, the wavelength in dielectric is shorter. Hence the diameter of the applicator in wavelengths remains constant throughout transition.

However, although such a applicator is perfectly satisfactory, the applicator bandwidth is comprised by the resonance found in the long length of dielectric filled waveguide. This means that any change in frequency generated by the microwave source could make a significant difference in applicator efficiency.

SUMMARY OF THE INVENTION

According to the present invention, there is provided a microwave applicator for applying electromagnetic radiation at microwave frequency comprising a coaxial input for receiving and passing a microwave signal input of predetermined frequency, a waveguide for receiving and propagating the microwave signal input, dielectric material positioned within the waveguide and extending beyond the waveguide to form an antenna for radiating microwave energy, characterised in that the coaxial input has means for providing a direct, in-line transition of the microwave signal input into the dielectric-filled waveguide.

Preferably, this direct in-line transition is achieved by the central conductor of the coaxial input extending axially centrally into the waveguide so as to excite microwaves in the waveguide. A lateral conductor extends radially from the central conductor towards the outer wall of the waveguide and serves to assist the launch of the microwaves into the waveguide in the appropriate mode for transmission to the tip.

Preferably, the applicator includes a temperature sensor which is directly connected to the coaxial input to minimise wiring.

Suitable, where the applicator is to be used for medical treatment such as endometrial ablation, it is important that the applicator be sterile for each use. Accordingly, preferably the applicator is coated with a microwave transparent coating allowing the applicator to be cleaned in conventional manner.

Although the microwave applicator of the present invention may be used for any desired application, it is preferred that it be used for endometrial ablation. This requires applying microwave energy to the applicator at a frequency which will be substantially completely absorbed by the endometrium, monitoring the operating temperature to ensure that the endometrium tissue is coagulated evenly through the uterine cavity, thus maintaining the application of the microwave energy for a period of time sufficient to destroy the cells of the endometrium.

The use of microwave power to heat the endometrium has two main advantages. Firstly, electromagnetic radiation at microwave frequencies is strongly absorbed by tissue and at around 8–12 GHz all microwave power is absorbed in a layer of tissue about 5 mm thick and it is impossible for microwave heating to extend beyond this region. This is ideal for the treatment of the endometrium which is about 5 mm thick. Secondly, because of this strong absorption, the amount of power required to achieve the desired temperature is relatively small.

Moreover, the improved applicator of the present invention has the following major advantages over the applicator previously disclosed in our aforementioned earlier application:

(i) the waveguide is shorter because, by forming a hybrid between a coaxial input and a dielectric filled waveguide, the distance between the transition and the radiating tip is very much shorter. This, in turn, reduces the amount of dielectric material necessary which improved band width and applicator efficiency; and (ii) it is possible to make the applicator flexible.

BRIEF DESCRIPTION OF THE DRAWINGS

The invention will now be described by way of example with reference to the accompanying drawings, in which:

FIG. 1 is a diagrammatic side elevation of a preferred microwave applicator in accordance with the invention; and FIG. 2 is a diagrammatic plan view of the waveguide of FIG. 1 showing the microwave fields.

DETAILED DESCRIPTION OF THE INVENTION

Figure 3:
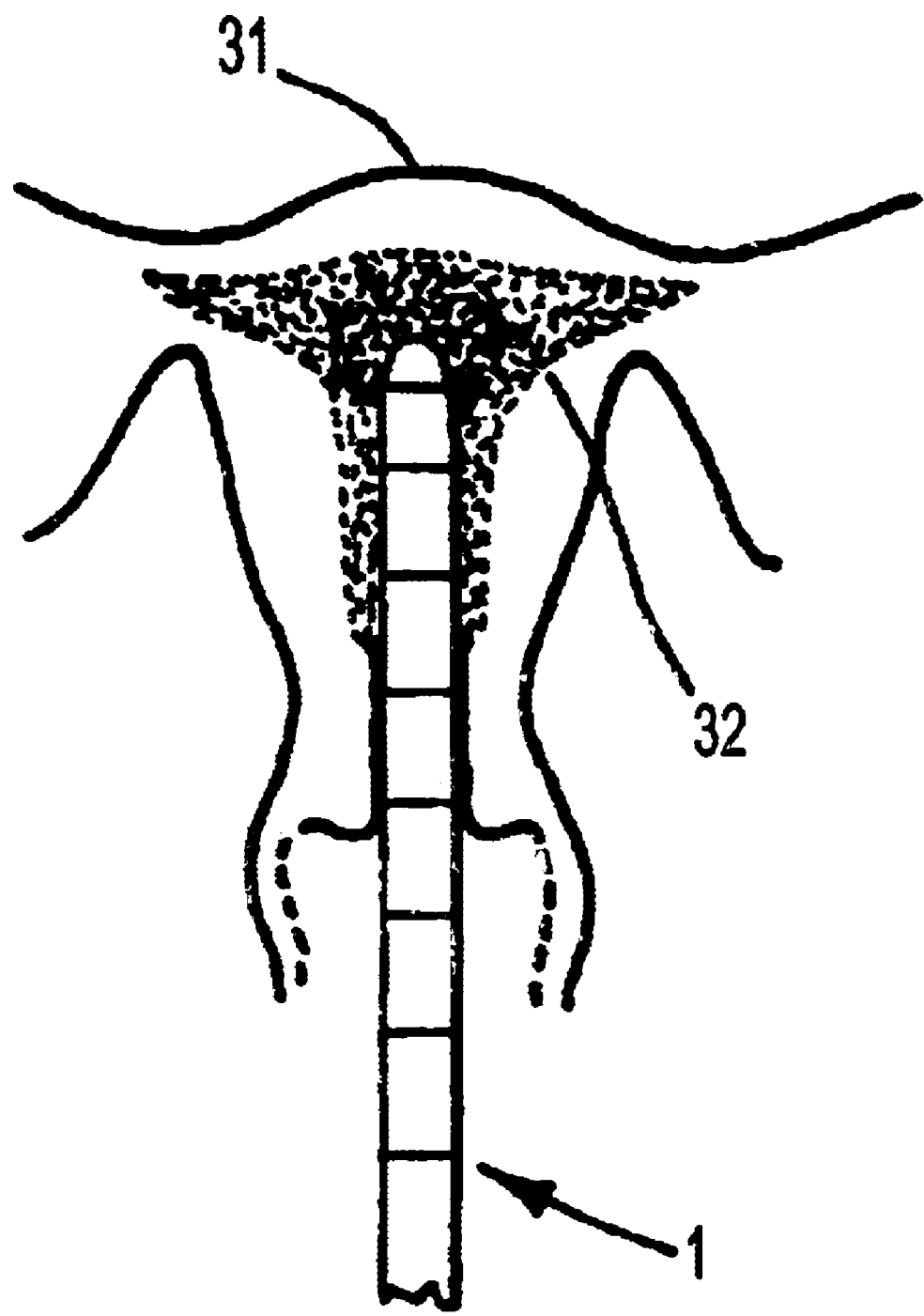
FIG. 3 shows the applicator used to perform endometrial ablation.

In FIG. 1, a microwave applicator (1) has a circular section waveguide (2) filled with a dielectric material (3). The waveguide (2) terminates short of the end of the applicator (1) and a portion (4) of the dielectric extends therefrom to form a radiating antenna tip for the microwave energy. That end of the waveguide remote from the tip (4), is connected to a coaxial cable (5) that powers the waveguide. The inner conductor (6) of the cable (5) extends axially into the dielectric (3) along the axis of the waveguide (2) so as to directly excite microwaves in the waveguide (2). The outer conductor (17) of the cable (5) is connected to the outer conductor wall (7) of the waveguide. The conductor (6) terminates within the waveguide, and a lateral conductor (8) extends radially from the conductor (6) through the outer wall (7) and serves to cause the microwaves to launch into the dielectric material (3) with the magnetic fields (14) and electric fields (15) oriented as shown in FIG. 2.

The coaxial cable (5) may be air-filled, but as illustrated in FIG. 1, it is filled with a dielectric (16), but this terminates short of the dielectric (3) of the waveguide (2) so as to leave an air gap (18) that accommodates axial expansion of the dielectric (16) when the applicator is heated in use, either during treatment or sterilisation.

The axial dimension L₁ of the air-gap (18), and the axial dimensions L₂ and L₃ of the conductor 6 within the waveguide (2) either side of the conductor (8), are all selected to tune out the reactance of the loop formed by the conductor (8), and thereby reduce backward reflections and enhance forwards launching of the microwaves in the waveguide.

The conductor (8) is insulated by insulation (9) as it passes through the outer waveguide wall (7).

Also shown in FIG. 1 is a thermocouple (10) on the outside of the radiating tip (4) for sensing the operating temperature. Moreover, in order to avoid additional wiring, the thermocouple (10) is directly connected by a connection 19 to the outer conductor (17) of the coaxial cable (5) at (11) and by a connection (20) outside the wall (7) to the central conductor (6) of the cable (5) via the lateral conductor (8) and a connection (12) at its outer end. Accordingly, the thermocouple signal passes out on the same coaxial cable (5) bringing the microwave power to the radiating tip (4). Conventional circuitry (not shown) is used to sense and extract the DC signal from the coaxial cable.

Although not shown, the applicator (1) is provided with a microwave-transparent protective coating of PTFE or other suitable material. The temperature sensing thermocouple (10) is provided between the coating and the dielectric material as well as being insulated from the dielectric material.

The preferred use of the applicator of the present invention as disclosed in our aforementioned published application number WO95/04385 where the applicator is supplied with a microwave frequency input in the microwave spectrum, preferably in the region of 8–12 GHz, from a microwave frequency generator source and amplifier.

FIG. 3 of the drawings shows the applicator 1 in use to perform endometrial ablation. The applicator is shown inserted into a uterus 31 with the tip 4 of the applicator in contact with the endometrium 32 within the uterus and transmitting microwave energy to produce local heating over a substantially spherical region 33 of the endometrium so as to destroy cells of the endometrium in this region.

What is claimed is:

1. A microwave applicator for applying electromagnetic radiation at microwave frequency, the applicator comprising:
    a waveguide with an outer waveguide wall enclosing dielectric material which extends beyond an output end of the waveguide wall to radiate microwave energy; and
    a coaxial input comprising an inner conductor and outer conductive sleeve surrounding said inner conductor for inputting a microwave signal of predetermined frequency at an input end of the waveguide, wherein the inner conductor extends from the outer conductive sleeve longitudinally within the waveguide wall into the dielectric material and terminates at a free end thereof within the dielectric material, and a lateral conductor is connected to, and extends laterally from, the inner conductor at a point within the dielectric material spaced a predetermined distance away from said free end so that the current flow in said inner conductor and lateral conductor launch microwaves in a fundamental mode within the dielectric material that travel to the output end of the waveguide.

2. A microwave applicator as claimed in claim 1, in which the inner conductor extends along the central axis within the waveguide.

3. A microwave applicator as claimed in claim 1, in which the lateral conductor extends as far as the waveguide wall.

4. A microwave applicator as claimed in claim 1, in which the lateral conductor is located in a central region along the length of the inner conductor within the waveguide.

5. A microwave applicator as claimed in claim 4 in which the lateral conductor extends through an aperture in the waveguide wall and is electrically insulated from the waveguide wall.

6. A microwave applicator as claimed in claim 1, in which the coaxial input is a dielectric filled cable in which the dielectric of the dielectric filled cable terminates short of the waveguide to leave an air-gap.

7. A microwave applicator as claimed in claim 1, in which a sensor is mounted on the applicator, and the sensor signal output is connected to the coaxial input.

8. A microwave applicator as claimed in claim 1, which is adapted for medical use.

9. A microwave applicator as claimed in claim 8 which is adapted for use as an ablator.

10. A microwave applicator as claimed in claim 1 in which the waveguide is a circular section waveguide.

11. A microwave applicator as claimed in claim 1 in which the lateral conductor is connected to the inner conductor at a position so as to enhance transfer of microwave energy to the waveguide.

12. A medical microwave applicator for applying electromagnetic radiation to a target mass of biological tissue at microwave frequency, the applicator comprising:
    a waveguide with an outer waveguide wall enclosing dielectric material that extends beyond an output end of the waveguide wall and is configured to radiate microwave energy; and
    a coaxial input comprising an inner conductor and outer conductive sleeve surrounding said inner conductor configured to input a microwave signal at an input end of the waveguide that is of a frequency that will cause emitted microwave energy to be absorbed by the target mass of tissue, wherein the inner conductor extends from the outer conductive sleeve longitudinally within the waveguide wall into the dielectric material and terminates at a free end thereof within the dielectric material, and a lateral conductor is connected to, and extends laterally from, the inner conductor at a point within the dielectric material spaced a predetermined distance away from said free end so that the current flow in said inner conductor and lateral conductor launch microwaves in a fundamental mode within the dielectric material that travel to the output end of the waveguide.

13. A medical microwave applicator as claimed in claim 12, in which the coaxial input is configured to input a microwave signal at the input end of the waveguide that is of a frequency that will cause emitted microwave energy to ablate the target mass of tissue.

14. A method for ablating biological tissue in a body, the method including the steps of:
    providing a microwave applicator comprising a waveguide with an outer waveguide wall enclosing dielectric material that extends beyond an output end of the waveguide wall and is configured to radiate microwave energy, and a coaxial input comprising an inner conductor and outer conductive sleeve surrounding the inner conductor for inputting a microwave signal of predetermined frequency at an input end of the waveguide, wherein the inner conductor extends from the outer conductive sleeve longitudinally within the waveguide wall into the dielectric material and terminates at a free end thereof within the dielectric material, and a lateral conductor is connected to, and extends laterally from, the inner conductor at a point within the dielectric material spaced a predetermined distance away from the free end so that the current flow in the inner conductor and lateral conductor launch microwaves in a fundamental mode within the dielectric material to the output end of the waveguide;

positioning the applicator in sufficiently close proximity to a target biological tissue mass to cause the tissue mass to absorb microwave energy emitted from the applicator; and causing the applicator to emit electromagnetic radiation at a predetermined microwave frequency that will cause the target tissue mass to absorb the microwave energy.

15. The method of claim 14 in which the step of positioning the applicator includes inserting the applicator into a body cavity leading to the target tissue mass.

16. The method of claim 15 in which:

the step of inserting the applicator includes positioning the applicator in sufficiently close proximity to an endometrium to cause endometrial tissue of the endometrium to absorb the microwave energy; and the step of causing the applicator to emit includes causing the applicator to emit radiation at a microwave frequency that will cause endometrial tissue to ablate.

17. The method of claim 16 in which the step of causing the applicator to emit includes the step of causing the applicator to emit microwave radiation at 8–12 GHz.

* * * * *